United States Patent [19]

Bayless et al.

[11] Patent Number: 5,188,609
[45] Date of Patent: Feb. 23, 1993

[54] SWIVEL CLIP MEDICAL TUBE HOLDER

[75] Inventors: Brian Bayless, Huntington Beach; Russell R. Lyon, Ramona, both of Calif.

[73] Assignee: Bryman Medical Inc., Fullerton, Calif.

[21] Appl. No.: 726,947

[22] Filed: Jul. 8, 1991

[51] Int. Cl.⁵ ............................................. A61M 5/32
[52] U.S. Cl. .................................... 604/180; 604/174
[58] Field of Search ............... 604/180, 179, 178, 174; 128/DIG. 6, DIG. 26; 24/16 PB, 304, 543; 248/70, 74.2, 316.7

[56] References Cited

U.S. PATENT DOCUMENTS

| | | | |
|---|---|---|---|
| 1,664,716 | 4/1928 | Wilberg | 24/543 |
| 2,528,095 | 10/1950 | Ward | 604/174 X |
| 3,473,768 | 10/1969 | Piasecki | 24/16 PB X |
| 3,535,746 | 10/1970 | Thomas, Jr. | 24/30.5 T |
| 3,556,575 | 1/1971 | Farkas | 24/16 PB X |
| 3,782,388 | 1/1974 | Page | 24/304 X |
| 4,057,066 | 11/1977 | Taylor | 128/DIG. 26 X |
| 4,484,378 | 11/1984 | Kimura et al. | 24/16 PB X |

Primary Examiner—Gene Mancene
Assistant Examiner—Jeffrey A. Smith
Attorney, Agent, or Firm—G. Donald Weber, Jr.

[57] ABSTRACT

A holder for securely, but removably, attaching a medical tube to the body of a patient. The holder comprises a clip releasably connectable to the medical tube, a base for supporting the clip and a connecting component for connecting the clip to the base. An adhesive pad can be associated with the base to secure the holder to the patient.

11 Claims, 1 Drawing Sheet

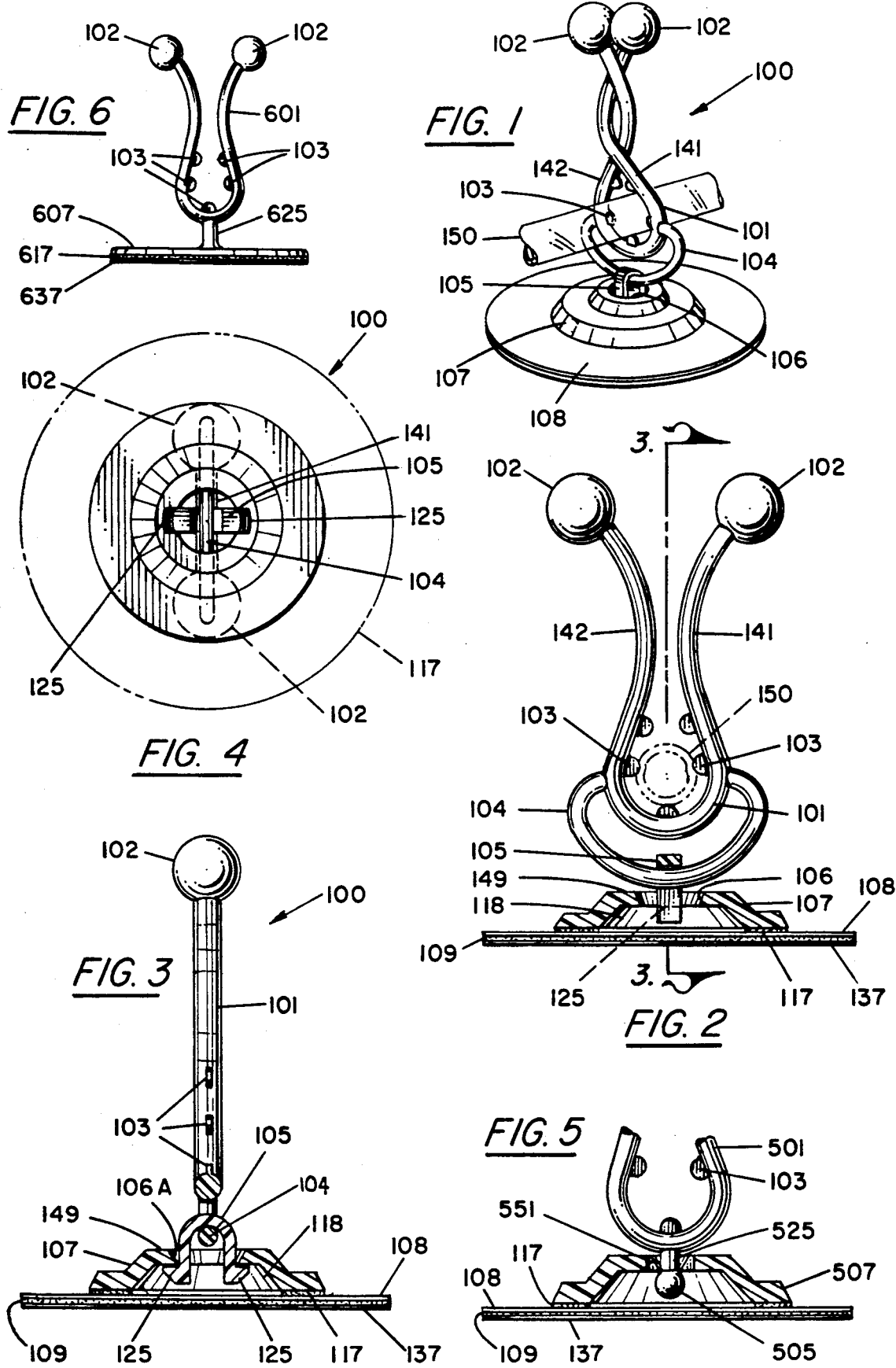

SWIVEL CLIP MEDICAL TUBE HOLDER

BACKGROUND OF THE INVENTION

1. Field of the Invention

The present invention relates to a holder for a medical tube, in general, and to a holder for attaching a medical tube to the body of a patient in order to enhance patient comfort and safety during medical procedures, in particular.

2. Prior Art

Many medical and surgical procedures require drainage and/or injection tubes to be applied to a patient. These tubes include tubes such as Foley catheters, bladder catheters, nose tubes, drainage tubes, intravenous tubes, cannulas, and the like. In use, such tubes extend from the body of the patient to a fluid source or drainage receptacle. It is frequently necessary to provide support for the tubes along the length thereof. This support is intended to prevent dislodging of the tube or fittings from the respective locations with regard to the patient and/or the source/drain units.

Typically, in the past, the procedure has been to support the medical tube by taping the tube directly to the body of the patient. Of course, the tube can be attached to splints or other devices which are also mounted on the body of the patient. As a result of these prior types of mountings, the connection and the mounting is extremely rigid and quite inflexible. This rigid, inflexible connector becomes more uncomfortable the longer it remains in place. Thus, it is a frequent source of complaints by the patient. Moreover, the patient frequently moves and, deliberately or inadvertently, causes the medical tube or fitting to become dislodged. Obviously, when the tube or fitting is dislodged, leakage or drainage can occur. Such leakage or drainage is frequently hazardous to the patient. In addition, it is wasteful of the materials which are to be provided to the patient. On the other hand, it is frequently unsanitary and, at least, unpleasant if the bodily fluids are discharged into the wrong location. The medical problems associated therewith such as infection and the like are clear.

Moreover, the utilization of tape directly on the body of the patient frequently causes rashes, inflammation and/or bed sores which are unpleasant to the patient and potential sources of infection or the like. The removal of this tape is another source of discomfort to the patient.

A more suitable method of mounting the tubing to the patient so that the disadvantages are overcome is clearly necessary.

PRIOR ART STATEMENT

The results of a preliminary patentability search are listed herewith. The patents uncovered during the search are listed in descending numerical order without any specific ranking thereof.

U.S. Pat. No. 4,915,694; ANTIMICROBIAL WOUND DRESSING AND SKIN FIXATOR FOR PERCUTANEOUS CONDUITS; R. Yamamoto et al. This patent is directed to an antimicrobial catheter shield which comprises an elastomeric catheter collar and a planar porous elastomeric peripheral flange with an absorbent patch which includes an antimicrobial agent attached to the flange opposite the collar.

U.S. Pat. No. 4,856,504; ANTIMICROBIAL WOUND DRESSING AND SKIN FIXATOR FOR ORTHOPEDIC PINS; R. Yamamoto et al. This patent is directed to an antimicrobial orthopedic pin percutaneous protection kit comprising the combination of a shield, a pad and a patch.

U.S. Pat. No. 4,660,555; OXYGEN DELIVERY AND ADMINISTRATION SYSTEM; H. Payton. This patent is directed to a system for supplying supplemental oxygen to a patient through a nose piece and an oxygen-tube holder wherein the tube holder is adapted to be mounted on an EKG electrode-type patch on a cheek prominence of the patient.

U.S. Pat. No. 4,360,025; CATHETER RETAINER; J. V. Edwards. This patent is directed to a catheter retainer which includes a plastic member having a central hole defined by a pair of resilient catheter-gripping jaws and a resilient catch member for holding the jaws in the relatively closed position.

U.S. Pat. No. 4,057,066; CATHETER HOLDER FOR SECURING A URETHRAL CATHETER TO A PATIENT; H. E. Taylor. This patent is directed to a holder for securing a urethral catheter to a patient. It includes an anchoring strip with a pressure-sensitive adhesive layer covered by a peel-off cover sheet and a cord which passes through a pair of adjacent openings in the anchoring strip.

U.S. Pat. No. 4,025,015; DETACHABLE ARTICLE-MOUNTING DEVICE; E. S. Kolic. This patent is directed to a mounting device which includes first and second adapters having separable plug-and-socket engagement to each other. One of the adapters includes a means for mounting the same to a relatively thick surface by adhesive means.

U.S. Pat. No. 3,728,388; MEDICAL TUBE HOLDER; S. J. Page. This patent is directed to an article for attaching a medical tube to the body of a patient and comprises a clip releasably connectable to the medical tube, a pad having adhesive on one side thereof for adherence to the body of the patient and a flexible, stretchable band connected between the clip and the pad.

U.S. Pat. No. 3,702,612; CATHETER SUPPORT; R. M. Schlesinger. This patent is directed to a catheter support which has a yoke attached to a base plate by a resilient beam capable of accommodating limited motion of the catheter without pulling the catheter from the patient. The base plate is adhesively backed for placement on the patient's body surface.

U.S. Pat. No. 3,146,778; CATHETER SUPPORT; H. A. Krawiec. This patent is directed to a catheter support which includes a pair of elements, one for holding the catheter and the other for securing to the body of the patient. The two elements are snapped together when support of the catheter is needed.

SUMMARY OF THE INSTANT INVENTION

This invention provides a holder for mounting a medical tube to the body of a patient. The holder prevents the easy dislodgment of all types of medical tubes such as IV tubes, catheters and the like from a patient while permitting increased comfort to the patient. The present invention eliminates the rigid, inflexible attachment technique of the prior art and replaces same with a holder which is swivelable so as to provide a substantial degree of freedom of movement between the medical tube and the body of the patient. By being able to swivel and pivot, the holder puts no undue pressure or stress on the skin site. This arrangement inhibits skin breakdown or trauma due to lack of strain and twisting on the skin site.

The tube holder of the instant invention includes a clip in the form of a flexible twist strap which can be readily locked or unlocked by merely twisting the respective ends thereof. A base for mounting on the patient's body is provided and can be adhered to the skin of the patient through a suitable adhesive. The clip is joined to the base in such a manner that permits the clip to swivel in relation to the base.

BRIEF DESCRIPTION OF THE DRAWINGS

FIG. 1 is a perspective view of a preferred embodiment of the holder of the instant invention.

FIG. 2 is a side view, partially broken-away, of the holder of the instant invention as shown in FIG. 1.

FIG. 3 is a cross-sectional view of the holder of the instant invention taken along the lines 3—3 in FIG. 2.

FIG. 4 is a cross-sectional view of the holder of the instant invention taken along the lines 4—4 in FIG. 2.

FIG. 5 is a partial cross-sectional view of a portion of another embodiment of the instant invention.

FIG. 6 is a side view of another embodiment of the instant invention.

DESCRIPTION OF THE PREFERRED EMBODIMENT

Referring now to FIG. 1, there is shown a perspective view of a preferred embodiment of the swivel holder 100 of the instant invention. The holder 100 includes a tube-retaining clip 101, an interlocking unit 105 and a base 107. In a preferred embodiment, a suitable adhesive patch 108 can be provided at the underside of base 107 for securing the holder 100 to the body of a patient.

More particularly, the clip 101 includes a generally U-shaped retainer (see FIG. 2) formed of a relatively thin, flexible strand of a suitable material such as nylon or the like. The strand includes an inherent "set" or hysteresis so that the ends thereof will securely engage when twisted together but will easily separate when untwisted. The strand should be able to endure several twist/untwist operations without breaking or losing resilience. The clip 101 includes the spherical ends 102 at or near the ends of the arms of the U-shaped retainer. The ends 102 are utilized to provide an interlocking relationship when the upper ends of the clip 101 are twisted and engaged. Ends 102 can take any shape or configuration desired. In fact, in some instances, the ends can be omitted. However, the ends 102 provide a more secure interlocking relationship between the arms of the clip 101.

The lower, closed portion of the clip 101 is configured to receive appropriate tubes 150 or the like. Depending upon the type of tube 150 to be utilized, different dimension clips 101 can be utilized so that the tube 150 can be retained within the clip 101 when twisted without producing any constriction in the tube.

In addition, a plurality of protuberances or bumps 103 may be formed on the inner edge of the strip which forms clip 101. These bumps can be used to grip and center the tube 150 within the space at the lower, closed end of the clip 101.

In a preferred embodiment, clip 101 includes a separate, closed loop 104 formed of the same material as the clip 101. The lower loop 104 is joined to the clip 101 at the sides of the closed portion of the clip. In a preferred embodiment, the extended diameter of the arc of the lower, closed end of clip 101 is used to define the connecting points for the ends of the lower loop 104. The lower loop 104 is arranged to be substantially uniformly spaced away from the bottom of the closed loop portion of clip 101. It is contemplated that lower loop 104 can be joined to clip 101 in any suitable configuration.

The clip 101 and the lower loop 104 can be joined together with any suitable process such as sonic welding or the like. Alternatively, the loop 104 and the clip 101 can be formed integrally during the fabrication process.

A bottom connector unit 105 is a substantially inverted U-shaped device which is adapted to engage the lower loop 104 by passing through the opening thereof. The ends of the U-shaped connector 105 include appropriate flanges, ledges or the like. These ledges or flanges extend outwardly from the outer surface of the U-shaped connector 105 (see FIG. 3).

The base 107 includes the raised central portion thereof which defines a dome-like cavity 118 which receives the ends of U-shaped connector 105. An aperture 116 is formed in the upper surface of the base 107. The ends of connector 105 pass through the aperture 106 into cavity 118. Specifically, the ends of the connector 105 are adapted to be squeezed together and inserted through the aperture 106 in the base 107. The connector 105 has sufficient hysteresis so that, when released, it expands within the aperture 106 whereby the flanges on the ends of connector 105 engage and slidably interlock with the undersurface of base 107.

Alternatively, the base 107 may be sufficiently flexible to permit the ends of connector 105 to pass through aperture 106, but sufficiently rigid to retain the connector 105 therein.

In either case, the ends of connector 105 are free to rotate about the center axis of connector 105 which passes through the aperture 106 of housing 107. Thus, the connector 105 can rotate through 360°. The clip 101, which is joined to connector 105, either directly or through loop 104, can, therefore, rotate through 360°, as well.

In a preferred embodiment, an adhesive layer 108 can be provided on the outer undersurface of base 107. Thus, the support device 100 can be mounted securely to a bed or a patient. The adhesive layer 108 is conventional and may include any suitable adhesive material 109 such as adhesive tape, a gel adhesive, or the like. A peelable liner 137 can be used with the adhesive layer.

Referring now to FIG. 2, there is shown a partially broken away side view of the holder 100. The generally U-shaped clip 101 is shown having a bell-lyre shape in the open, untwisted condition. That is, the arms 141 and 142 of the clip are curved toward each other to form a pair of sinuous arms which will easily entwine. Again, this curvature permits an improved interlocking relationship between the arms 141 and 142, with or without the ends 102. The lower, closed end of the U-shaped clip 101 includes any desired number of the protuberances or bumps 103. A tube 150 is shown, in dashed outline, to represent the operation of the clip in maintaining the tubing.

The ends 102 of the clip 101 are generally spherical in shape. Again, the end configurations can be of any desired shape or omitted altogether, as desired. The clip 101 is, as noted, fabricated of nylon (or other suitable medical grade material) and configured to have a degree of hysteresis so that when the arms are twisted, they tend to return to the original condition whereby the interlocking thereof is achieved.

The lower loop 104 is shown adjacent to the bottom of the closed end of clip 101. It is conceivable that the loop 104 could be reconfigured or even omitted in some instances. However, the loop 104 permits a greater degree of freedom of movement of the clip 101 relative to the connector 105, as is readily apparent. Moreover, the tube 150 does not interfere with movement of the clip 101. The clip 101 can move through approximately 180° from left to right when the loop 104 passes through the connector 105. As will be seen subsequently, the clip 101 can move through 180° when rotating in the plane of the Figure.

The base 107 is shown to have a relatively flat lower surface 117 with an upraised, dome-like center portion which produces a cavity or chamber 118 at the center portion of the base. This space in the chamber 118 is provided to receive the ends of the connector 105. The connector 105 (shown in cross-sectional view) is substantially U-shaped and engages the loop 104 of the clip 101. The connector 105 includes flanges 125 or ledges at the ends thereof. These flanges extend outwardly from the sides of connector 105 and engage the underside of the upraised central portion 149 of base 107. The aperture 106 passes through the base 107, typically, at the center of the dome 149. The connector 105 passes through the aperture 106 and is free to rotate through 360° relative to the base.

Referring now to FIG. 3, there is shown an edge view of the holder 100. In particular, there is shown a cross-sectional view of the clip 101 taken along the lines 3—3 in FIG. 2. The clip 101 (or catch) is shown as a relatively straight or planar component, as described above. The protuberances or bumps 103 are shown to be relatively thin and extending inwardly from the inner surface of the clip 101. As shown in FIG. 3, the clip 101 has a generally cylindrical configuration.

Likewise, the loop 104 which extends from clip 101 has a generally cylindrical configuration which is, in this embodiment, somewhat smaller in diameter. This is not a requirement of the device. However, it provides a somewhat greater degree of flexibility and movement of the clip 101.

The base 107 includes the upraised portion 149 thereof and the aperture 106 in the upper surface of the upraised portion. The U-shaped connector 105 includes the flanges 125 shown in FIG. 3. These flanges, as noted above, engage the undersurface of base 107 adjacent to aperture 106 so that the expanded connector 105 will not pass through the opening 106. Typically, the connector 105 has one end thereof passed through loop 104. The two ends of the U-shaped connector 105 are then squeezed together and passed through aperture 106. This can be enhanced by applying a bevel or chamfer to the side wall 106A of the opening 106. However, the upper surface of the flanges 125 engages the undersurface of the dome 149 in the base 107 so that the connector 105 does not pull out through the aperture 106. Moreover, as seen from the Figures, the connector 105 is free to rotate through 360° thereby carrying with it the clip 101 which also rotates through 360°.

Referring now to FIG. 4, there is shown a bottom view of the holder 100 of the instant invention wherein the clip 101 and other parts are shown in phantom outline. It is seen how the flanges 125 of the connector 105 engage with the undersurface of the dome 149 of base 107 to retain the items together. The relationship of the loop 104 and the clip 101 (including the end portions 102) is also clear from FIG. 4.

In operation, holder 100 may be used for attaching medical tube 150 to the body of a patient (not shown). Assuming for example, and as shown in FIG. 1, that tube 150 is a bladder drainage tube. Tube 150 is typically draped over one leg of the patient and connected thereto at two locations. To use holder 100, the removable protective sheet 137 is removed from the adhesive layer 108. The holder 100 is attached to the body of the patient, as desired. Thereafter, clip 101 is twisted (if necessary) and opened, in the manner shown in FIG. 2, to permit the insertion thereinto of tube 150. The clip 101 is then twisted and closed as shown in FIG. 1. Thus, clip 101 will securely grip tube 150, thereby restricting movement thereof. Such firm connection may result in many different ways. For example, the inner diameter of clip 101 may be made slightly smaller than the outer diameter of tube 150 so that a slight pinching action occurs. Alternatively, clip 101 may have a sticky surface thereof to achieve the same result. However, neither of these possibilities may be necessary because of the well known fact that a cylindrical member passing through a thin annulus, at an angle thereto, tends to be gripped by the inner edges of the annulus and to prevent axial motion relative thereto. The bumps 103 also tend to grip the tubing 150. If desired, the bumps 103 may comprise a tacky material.

The resultant attachment of tube 150 to the body of the patient greatly enhances patient comfort and safety during a variety of medical procedures. With holder 100, the rigid, inflexible attaching techniques of the prior art are eliminated and replaced by a holder having built-in multi-direction motion capability which permits relative movement between medical tube 150 and the body of the patient. As a result, slight patient movement is permitted without discomfort and skin breakdown or trauma. Moreover, the possibility of tube dislodgement is significantly reduced. Holder 100 is simple and may be manufactured and sold inexpensively so that it may be used only once and thereafter discarded.

Referring now to FIG. 5, there is shown another embodiment of the instant invention. In this embodiment, holder 500 is quite similar to holder 100 shown in FIG. 1. The clip 501 is substantially the same as clip 101. However, in this embodiment, a spherical knob 505 is formed at the closed end of clip 501. Preferably, a short neck 525 is interposed between clip 501 and knob 505.

The base 507 is substantially identical to base 107 and includes an aperture 506 through when knob 505 is inserted. If necessary, base 507 may include one or more cuts 551 extending radially outwardly from aperture 506 to provide flexibility for receiving knob 505. The clip 501 is free to rotate and pivot as before. The neck 505 permits a degree of freedom of movement even though the knob 505 remains trapped in the base 507.

Referring now to FIG. 6, there is shown a side view of another embodiment o the instant invention. In this embodiment, the holder 600 includes the clip 601 which is substantially identical to the clip 101 in FIG. 1. The twistable, U-shaped or lyre-shaped clip 601 is formed of a thin strand or filament of plastic, such as nylon. The clip is provided with a hysteresis or resilience which causes the clip to selectively assume a normal position and an engaged (twisted) position. The knobs 102 and bumps 103 are substantially the same as the similar components described supra.

In this embodiment, the base 607 can be similar to the base 107. However, the base 607 can be flatter than the base 107 in that an interior chamber is not required. Thus, the base 607 can be substantially planar. In the typical configuration, base 607 is a round, disk-like element.

The adhesive layer 617 and the peelable liner 637 are similar to the adhesive layer 109 and the liner 137 described supra.

In the embodiment of FIG. 6, however, the stem 625 interconnects the base 607 and the clip 601. Moreover, the stem, base and clip can all be formed of a unitary element. The stem 625 is formed of a relatively thin strand of material, e.g. nylon. The stem 625 is capable of bending approximately 90° in any direction. Thus, the clip can fold down onto the base 607 (or the supporting surface such as a patient's skin). Likewise, the stem 625 can twist around the vertical axis thereof by up to 180°. (The twist limitation is normally defined by the use of the holder rather than the construction of the stem.) The resilience of the material of the holder causes the holder to return to the original position when the stem returns to its original position.

Thus, there is shown and described a unique design and concept of a swivel clip medical tube holder. The particular configuration shown and described herein relates to a holder for IV tubing or the like. In a preferred embodiment, the holder is formed of a suitable plastic material such as nylon, polyethylene, Delrin or the like. However, any appropriate material can be used. Moreover, the holder can be formed in a one-piece or in a multi-piece configuration. While this description is directed to a particular embodiment, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

We claim:

1. A tubing holder comprising,
deformable retainer means for retaining tubing,
said deformable retainer means comprises a relatively thin strip of flexible material,
said strip is reversed upon itself to form a clip having a closed end and a pair of spaced apart, elongated arms,
said pair of elongated arms are arranged to be selectively engaged with each other thereby to close said clip,
base means, and
connector means for movably joining said deformable means to said base means,
said connector means is shorter than said deformable retainer means whereby said deformable retainer means is maintained in close proximity to said base means,
said connector means includes a loop means spaced apart from said deformable retainer means adjacent to the closed end thereof,
interlocking means adapted to encompass a portion of said loop means and engage said base means,
said interlocking means comprises a U-shaped strap which engages said loop means,
said U-shaped strap includes enlarged free ends for slidably engaging said base means.

2. The holder recited in claim 1 wherein,
said connector means joins said deformable means to said base means so as to permit said deformable means to move from a position perpendicular to said base means to a plurality of positions approximately parallel to said base means and any angle therebetween.

3. The holder recited in claim 1 wherein,
said base means includes a cavity for receiving and engaging said connector means.

4. The holder recited in claim 1 including,
adhesive means on the undersurface of said base means for adhering to a surface.

5. The holder recited in claim 1 including,
at least one gripping means provided on the surface of said deformable retainer means intermediate said elongated arms.

6. The holder recited in claim 5 wherein
said gripping means comprises a projection extending from said deformable retainer means.

7. The holder recited in claim 1 wherein,
the closed end of said deformable retainer means form a first smooth arc, and
said loop means form a second smooth arc at least a portion of which is substantially parallel to said first arc.

8. The holder recited in claim 1 wherein,
said base means includes an aperture therein for receiving at least a portion of said connector means.

9. The holder recited in claim 8 wherein,
said base means defines a cavity which receives said portion of said connector means through said aperture.

10. The holder recited in claim 1 wherein,
each of said pair of elongated arms has an enlarged end portion which enhances an interlocking relationship of said arms when engaged with each other.

11. The holder recited in claim 1 wherein,
said deformable retainer means is formed of a resilient material which tends to return to a normal position after said deformable retainer means has been deformed.

* * * * *